United States Patent
Benderev

(10) Patent No.: US 7,485,099 B2
(45) Date of Patent: Feb. 3, 2009

(54) SYSTEMS AND METHODS FOR DETERMINING PRESSURE AND SPACING RELATING TO ANATOMICAL STRUCTURES

(76) Inventor: Theodore Benderev, 26975 Magnolia Ct., Laguna Hills, CA (US) 92653

( * ) Notice: Subject to any disclaimer, the term of this patent is extended or adjusted under 35 U.S.C. 154(b) by 425 days.

(21) Appl. No.: 10/666,396

(22) Filed: Sep. 18, 2003

(65) Prior Publication Data

US 2005/0065408 A1    Mar. 24, 2005

(51) Int. Cl.
- A61B 5/103 (2006.01)
- A61B 5/117 (2006.01)
- A61B 5/22 (2006.01)
- A63B 21/00 (2006.01)
- A63B 21/008 (2006.01)
- G01L 5/00 (2006.01)
- A61M 1/00 (2006.01)
- A61M 31/00 (2006.01)
- A61M 37/00 (2006.01)
- A61M 29/00 (2006.01)

(52) U.S. Cl. ........... 600/587; 600/591; 600/593; 604/27; 604/66; 604/93.01; 604/98.01; 604/98.02; 604/103.05; 73/379.08; 73/379.09

(58) Field of Classification Search .......... 600/587, 600/591, 593; 604/27, 66, 93.01, 98.01, 604/98.02, 103.05; 73/379.08, 379.09
See application file for complete search history.

(56) References Cited

U.S. PATENT DOCUMENTS

| | | | |
|---|---|---|---|
| 5,353,800 A | 10/1994 | Pohndorf et al. | |
| 5,477,860 A | 12/1995 | Essen-Moller | |
| 5,752,522 A * | 5/1998 | Murphy | 600/587 |
| 5,899,927 A | 5/1999 | Ecker et al. | |
| 6,033,366 A | 3/2000 | Brockway et al. | |
| 6,251,093 B1 * | 6/2001 | Valley et al. | 604/97.03 |
| 6,296,615 B1 * | 10/2001 | Brockway et al. | 600/486 |
| 6,379,308 B1 | 4/2002 | Brockway et al. | |
| 6,401,520 B1 | 6/2002 | Volkwein et al. | |
| 7,025,772 B2 * | 4/2006 | Gellman et al. | 606/151 |
| 2001/0034501 A1 | 10/2001 | Tom | |
| 2004/0102722 A1* | 5/2004 | Naghavi | 600/587 |

FOREIGN PATENT DOCUMENTS

WO    WO 9901740 A1    1/1999

* cited by examiner

Primary Examiner—Max Hindenburg
Assistant Examiner—Jeffrey G Hoekstra
(74) Attorney, Agent, or Firm—Stetina Brunda Garred & Brucker

(57) ABSTRACT

Systems and methods for measuring the pressure exerted between or within anatomical masses/structures, as well as the position and/or spatial dimensions of an anatomical structure. According to a preferred embodiment, the invention comprises a sensor element positionable between anatomical structures or within an anatomical structure. The sensor is operative to generate a signal indicative of the pressure being exerted therebetween or therewithin. The sensor may be operative to measure spatial dimensions between structures or within a structure. A monitor coupled to the sensor receives a signal generated thereby and provides an indication as to the spacing or pressure being measured. The systems and methods may be utilized in diagnostic tests or surgical procedures.

8 Claims, 3 Drawing Sheets

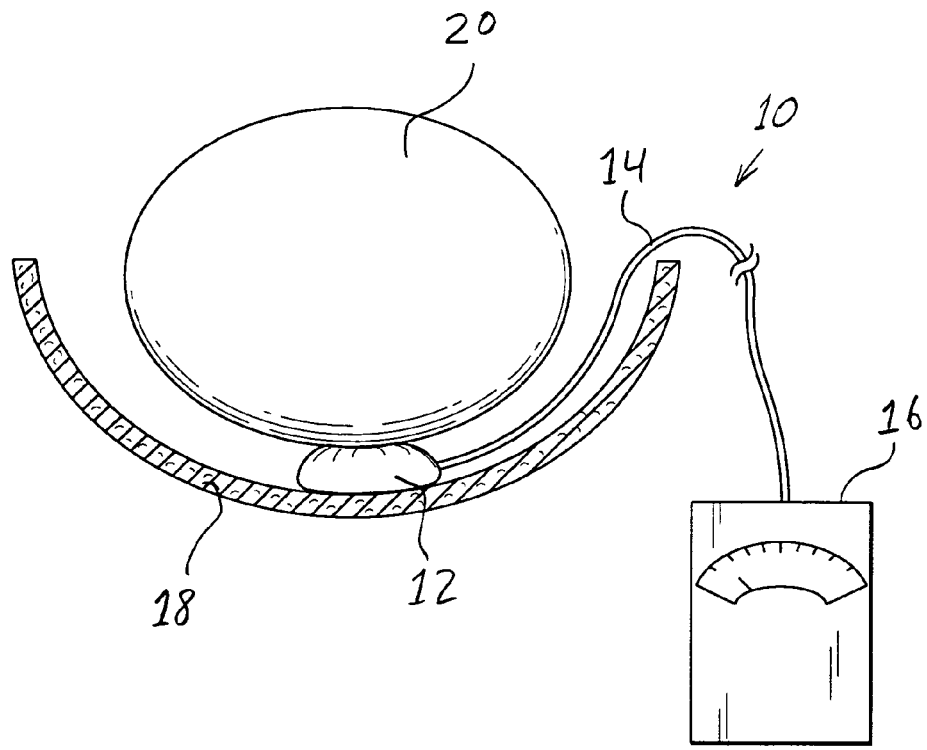
FIG. 1
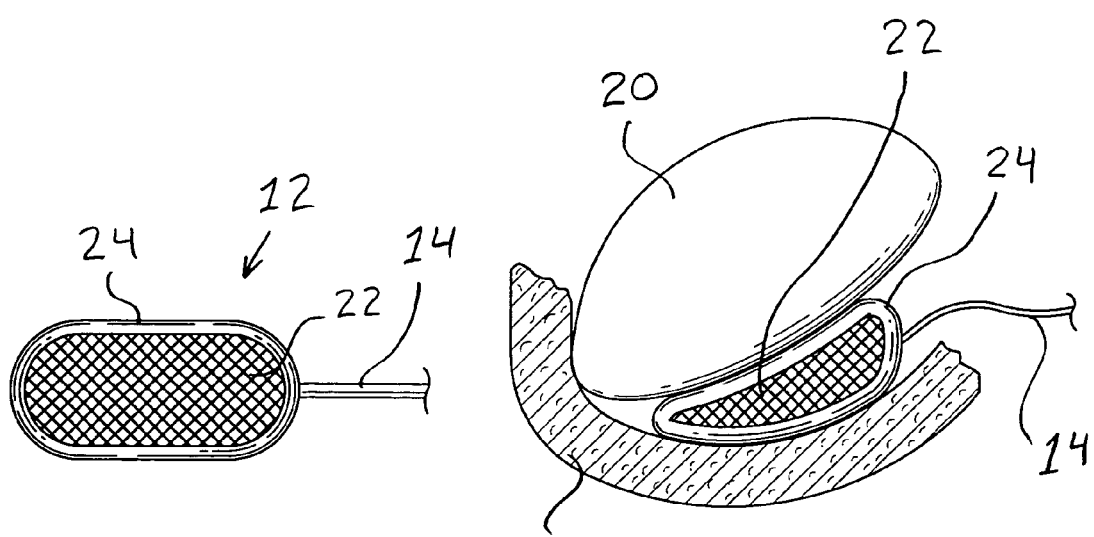
FIG. 2a  FIG. 2b

SYSTEMS AND METHODS FOR DETERMINING PRESSURE AND SPACING RELATING TO ANATOMICAL STRUCTURES

CROSS-REFERENCE TO RELATED APPLICATIONS

The following application claims priority to Disclosure Document Number 520388 which was filed Oct. 23, 2002, the teachings of which are herein incorporated by reference.

STATEMENT RE: FEDERALLY SPONSORED RESEARCH/DEVELOPMENT

Not Applicable

BACKGROUND OF THE INVENTION

The relative positioning and pressure exerted by and between anatomical masses, structures, implants, and the like are often times crucial in assessing a patient's condition and making a proper diagnosis. In this regard, it is often of particular interest to determine the degree of pressure being exerted upon or by a particular type of anatomical structure, as well as whether or not the positioning of one or more structures is maintained in a proper orientation. For example, it is often ideal to measure the pressure capable of being exerted by either the urethral or anal sphincter, to thus assess sphincter tone, in making a diagnosis of urinary or fecal incontinence. It is likewise often desirable to measure a patient's urethral pressure profile to thus measure urethral resistance to outflow of urine or to measure abdominal or bladder leak point pressure. Further areas where such need arises include the monitoring of intercranial pressure for patients with hydro-encephalitis or head injuries, intramuscular compartment pressure for patients with compartment syndrome, intraesophageal pressure for patients being evaluated for gastroesophageal reflux disease (GERD), and intravascular pressure to assess blood pressure. Still further examples include needs that often arise with respect to intra-cavitary uses such as bladder, intra-pleural and intra-abdominal pressure.

In addition to the frequent need to measure the pressure and/or spatial relationship in or between anatomical masses/structures, implants, and the like, is the need to measure and determine physiological pressures and relative spacing between anatomical masses/structures during specific types of surgical procedures, and in particular surgical procedures incorporating the use of slings, grafts, and the like for supporting and separating anatomical structures and tissue masses. Such procedures are well known in the art and include, among numerous others, pubovaginal sling surgery, the specific aspects of which are set forth in Applicant's issued U.S. Pat. No. 6,050,937, issued on Apr. 18, 2000 entitled SURGICAL TENSION/PRESSURE MONITOR and U.S. Pat. No. 6,302,840, issued on Oct. 16, 2001 entitled SURGICAL MONITOR, the teachings of which are expressly incorporated herein by reference. Additionally exemplary of such procedures include fundoplication, a procedure well known in the art for mobilizing the lower end of the esophagus and plication of the fundus of the stomach around it (i.e., fundic wrapping) in the treatment of reflux esophagitis that may be associated with various disorders, such as hiatal hernia.

In both such procedures, it is necessary to maintain proper support and orientation of a particular anatomical structure. In the case of pubovaginal sling surgery, optimal positioning of the sling relative the urethra, as well as the degree of tension imparted by the sling to the urethra, must be achieved in order to attain a favorable patient outcome. Likewise, in the case of fundoplication, optimal positioning of the fundus relative the esophagus must be made in order to obtain a successful outcome.

The foregoing examples are merely two of a wide variety of procedures performed that place great demands on the surgeon to not only securely attach a given tissue, sling, graft and the like into position, but to also position the same so that it offers the desired/selective support. The latter aspect is particularly difficult insofar as there is generally lacking in the art any type of mechanism by which a surgeon can know with certainty when a given tissue, sling or graft is optimally positioned and/or imparts the necessary support. Indeed, most surgeons only acquire such skill through substantial experience and that new, inexperienced surgeons typically produce substantially less favorable outcomes due to their inability to know when or how to affix an implant, tissue, sling or graft such that the same is optimally positioned.

In an attempt to address such shortcomings, at least one product, namely, the T-DOC air-charged catheters produced by T-Doc Company. of Mt. Laurel, N.J., has been developed to provide pressure-sensing measurements. Essentially, such device comprises a catheter-deployed balloon requiring an injection of air which thus produces an "air-charge" baseline of pressure. Once properly positioned for the applicable procedure (i.e., urodynamic procedures), changes in the physiologic pressure that occur at a particular site are transmitted through a micro-volume of trapped air in the T-DOC catheter. Another intent for use in applications involving the diagnosis of laryngopharyngeal reflux has been the Medtronic response catheter system that measures reflux at the lower esophageal level at the level of the esophageal inlet. Such system is operative to span the distance about the esophageal inlet.

Such systems, however, are complex and difficult to accurately deploy. Moreover, the T-DOC system requires specialized transducer docking cables and further relies upon sophisticated and expensive componentry that, in certain applications, can produce unreliable results. Also, the T-DOC system in certain applications is difficult and time consuming to deploy. The latter aspect is particularly problematic insofar as to the extent such catheter-based system is unnecessarily prolonged or if a given procedure cannot be scheduled within a requisite amount of time, patient in need of such procedure (i. e., the performance of a urodynamic profile) might be prone to more infections and pain from the possible need for extra catheterization.

Accordingly, there is a substantial need in the art for a system and procedure which provides accurate and reliable data regarding the measurement of physiological pressures that may be exerted within a cavity or tube;, especially in relation to routinely performed procedures such as urodynamic procedures. There is likewise a substantial need in the art for a system and procedure providing accurate and reliable data related to the measurement of physiological stresses and pressures exerted between anatomical masses/tissues and structures, implants, and the like, as well as the relative spatial positioning of one or more anatomical structures to thus enable a physician to properly evaluate a particular condition of a patient. There is likewise a need in the art for such a system and procedure that has widespread application over a variety of physiological pressure/spatial parameters that are useful in assessing a wide variety of medical conditions.

There is likewise a need in the art for such a system and method that are operative to provide a surgeon during the performance of an operation involving the fixation of an implant, tissue, sling or graft into position with an indication as to when such implant, tissue, sling or graft is optimally fixed into position relative an anatomical structure, and that further quantifies the amount of tension or pressure being imparted by the sling or graft to the anatomical structure, and/or may further provide an indication of the relative positioning of the implant, tissue, sling or graft to such structure. There is further lacking in the art a system and method that, in addition to identifying the amount of tension and pressure imparted by a given sling or graft upon an anatomical structure and a relative spatial positioning therebetween, also provides an indication as to the optimal parameters of tension or spatial relationship of the sling relative such anatomical structure. Still further, there is a need for such systems and methods that can be deployed such that a higher number of favorable patient outcomes is attained.

BRIEF SUMMARY OF THE INVENTION

The present invention specifically addresses and alleviates the above-identified deficiencies in the art. In this regard, the present invention is directed to systems and methods for measuring physiological pressures exerted within or between anatomical masses/structures, implants and the like for use in evaluating a patient's condition, particularly with respect to determining intra-luminal and intra-compartmental pressures and compressive pressures exerted against adjacent structures. The present invention further includes systems and methods for determining spacing and orientation of an anatomical structure or the positioning of an anatomical structure relative at least one other anatomical structure. More particularly, the systems and methods of the present invention may be adapted and configured to obtain measurements of intraurethral, intraanal, intraabdominal, intracranial, intraesophageal or intravascular physiological pressures, as well as physiological pressures exerted within intramuscular compartments and compressive forces exerted between anatomical masses/structures, implants, and the like. The systems and methods are further operative to provide measurements related to the spatial positioning of such anatomical structures, as well as the relative spatial positioning and orientation of an anatomical structure relative at least one second anatomical structure.

In further refinements of the present invention, there are provided systems and methods for measuring and identifying the tension or pressure exerted by a given implant, tissue, sling, graft, and the like, and/or the resultant pressure exerted thereby upon a given anatomical mass/structure during the fixation of such sling, graft, etc. during a given procedure. The present invention is further preferably directed to systems and methods that provide a surgeon performing any such type of procedure with an indication as to the optimal degree of tension or spatial relationship a sling, tissue, graft, and the like possesses relative a given anatomical structure, as well as systems and methods that enable the surgeon to secure such sling or graft at such optimal tension/position relative a given anatomical structure.

According to the preferred embodiment, the invention comprises the combination of a sensor for measuring the pressure and/or the specific contours and spacing within a body cavity, such as the lumen of a tube/sphincter, along with a monitor or meter coupled thereto. It is contemplated that the monitor or meter may be constructed to be portable in nature, and designed for either single or repeated usage. Alternatively, or in addition to measuring spacing and pressure, the sensor may be operative to determine the tension between two or more structures and/or volume or pressure intracavity or within a tissue. The sensor is preferably insertable within an anatomical mass or structure, such as the lumen of a tube or body cavity, such as the urethra or bladder, or otherwise interposable between two anatomical masses/structures, which may comprise any surgical implant, organ or synthetic material, and may include any type of sling, graft, or other material or tissue utilized to support an anatomical object such as the urethra or bladder. Such sensor is operative to detect and quantify the pressure exerted within or between such anatomical masses/structures. Otherwise, the sensor will measure the pressure exerted by a target structure, such as a sphincter, or within an internal compartment, such as an intraluminal passageway or intramuscular compartment. The sensor may further be designed to measure the pressure of a fluid thereagainst, as it is expressly contemplated that the sensors and monitors of the present invention will be utilized in urodynamic profile procedures and operative to measure the pressure or urine flow capable of being exerted by the bladder. Still further, the sensor and monitor will be operative to measure the distance between two anatomical masses/structures as may be desired in procedures that optimally place some degree of spacing between such objects.

Such sensor may comprise a balloon-like outer membrane (sack) within which may be disposed a material operative to support the membrane to maintain a specific volume or to maintain a generally expansive state. In addition, the inner material will be operative to measure the degree of pressure exerted about the exterior of the balloon or the spatial dimensions of the balloon, especially when the same is compressed to have a reduced volume. In preferred embodiments, the balloon will incorporate therein a lattice structure operative (maintain having a specific baseline volume or keep the balloon inflated) The lattice structure that will be operative to selectively collapse once a threshold amount of pressure is applied thereto. Depending on the application, the lattice structure may collapse completely once a predetermined amount of pressure is applied thereto, or may alternatively collapse in incremental amounts upon application of incrementally higher amounts of pressure exerted externally about such balloon-sack. Alternatively, such balloon will have a quantity of sponge-like material, and in particular a compression foam disposed therein, that is operative to compress and decrease in size upon the application of a pre-determined amount of pressure externally about the balloon. Such balloon may further comprise an air or fluid-filled balloon that selectively deforms upon the application of an external amount of pressure applied thereto. Such embodiments may be further configured to determine spatial positioning and orientation based upon measurable distances within and about the dimensions of the balloon.

The monitor or meter coupled to the sensor provides a visual indication of the pressure that is being exerted between the target anatomical masses/structures, and/or, alternatively, the pressure exerted within a lumen, cavity or compartment. The monitor may further be adapted to provide a visual indication of the spatial relationship between anatomical masses/structures to thus enable the surgeon to manipulate and optimally position a particular object, such as an implant, tissue, sling or graft (i.e., set at tension levels and/or fixed distances and orientations from the anatomical mass/structure). In a further refinement, such meter additionally provides the surgeon with an indication as to when the implant, tissue, sling or graft pressure or placement has obtained ideal levels indicative of a favorable patient outcome so as to enable the surgeon to secure the same in position in such a manner that an ideal pressure or anatomical support is maintained. As discussed above, it will further be understood that the monitor may be portable in nature and may be configured for either single or repetitious usage.

BRIEF DESCRIPTION OF THE DRAWINGS

These as well as other features of the present invention will become more apparent upon reference to the drawings.

FIG. 1 is a perspective view of a system for measuring pressure between an anatomical mass and an anatomical structure, as constructed in accordance with a preferred embodiment of the present invention.

FIG. 2a is a perspective view of a sensor incorporated within the systems of the present invention, the sensor element having a lattice structure disposed therein assuming a first expansive configuration.

FIG. 2b is a perspective view of the sensor depicted in 2a as disposed between an anatomical mass and an anatomical structure, said lattice structure being selectively shown collapsing in an amount indicative of the pressure exerted between the anatomical mass and the anatomical structure.

DETAILED DESCRIPTION OF THE INVENTION

Figure 3A:
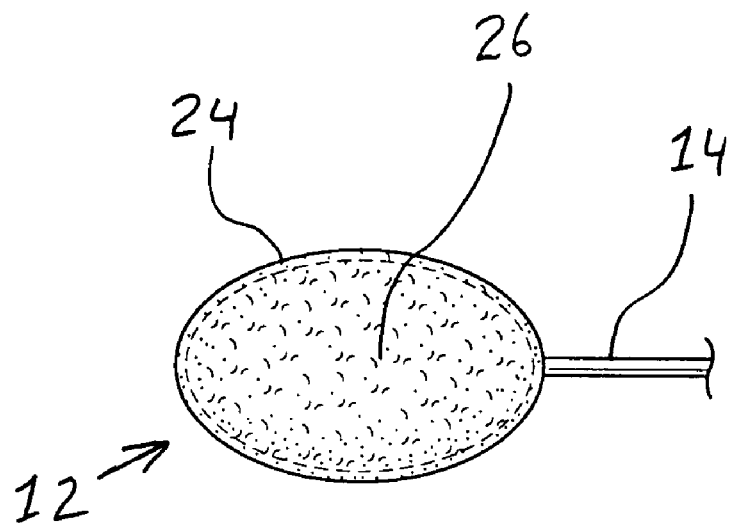
FIG. 3a is a perspective view of a sensor constructed in accordance with a preferred embodiment of the present invention shown assuming a first expansive configuration.

The detailed description as set forth below in connection with the appended drawings is intended as a description of the presently preferred embodiments of the invention, and is not intended to represent the only form in which the present invention may be constructed or utilized. The description sets forth the functions and sequences of steps for constructing and operating the invention in connection with the illustrated embodiments. It is understood, however, that the same or equivalent functions and sequences may be accomplished by different embodiments and that they are also intended to be encompassed within the scope of this invention.

According to the first embodiment shown in FIG. 1, the surgical monitoring device 10 comprises a pressure or contact sensor 12 interposable between anatomical masses and/or anatomical structures 18, 20. The sensor 12 is operatively coupled via link or connection 14 to a monitor 16, the latter being operative to provide an indication as to the degree of stress, tension, pressure and/or spatial relationship existing between the anatomical masses/structures of within a specific anatomical structure, whether it be the lumen of a tube, compartment or bodily cavity. As should be recognized at the outset, the term anatomical structure or anatomical mass as used herein is to be construed as broadly as possible to include any and all organs, tissues, bones and/or implants. It should further be understood that anatomical structure may apply to any medical device, tissue, or material, whether natural or synthetic, which may need to be properly positioned, stabilized or supported within or upon the body.

The sensor 12 may take the form of any of a variety of those well known to those skilled in the art that are operative to measure either the spatial separation between the anatomical mass and structure and/or the compressive force, stress or pressure exerted therebetween to generate a signal correspondingly thereto. To that end, although any of a number of sensors are known in the art and are commercially available that can readily identify and measure the distance and/or pressure exerted between the anatomical masses and structures, it is contemplated that in one preferred embodiment the sensor will comprise a deformable or non-deformable balloon or elastic sack-like member operative to assume a first open state when on baseline amount of pressure, such as atmospheric pressure such that the balloon or sack maintains a first relatively static volume.

To maintain such relatively static or fixed volume, it is contemplated that the balloon will be filled with a supportive material within the sack, which may preferably comprise a lattice structure, preferably formed from plastic or other like material, that is operative to collapse in a pre-determined volumetric amount once a baseline amount of pressure is applied externally about all or a portion of the balloon member and thereafter collapse in incremental amounts to the extent proportionately higher increments of pressure is exerted about all or a portion of the balloon. The ability to fabricate such collapsible lattice may be accomplished by any of a variety of designs well-known to those skilled in the art, and can be selectively fabricated such that such lattice may be caused to selectively collapse at predetermined intervals where a corresponding amount of pressure is applied thereto, as imparted by an external force applied to the balloon or sack within which the lattice is disposed. Such lattice structure may further be fabricated such that the same can selectively collapse at precise points where a specific amount of threshold pressure is applied thereto.

An example of such lattice structure is illustrated in FIGS. 2a-2b, wherein FIG. 2a shows a lattice structure 22, as encapsulated within a balloon-type sack 24, assuming a first open or non-compressed configuration suitable for placement between two anatomical masses/structures. Since no pressure (i.e., other than a baseline amount of pressure, such as atmospheric pressure) is being applied to such lattice structure 22, the same will remain in such open state indefinitely. As illustrated in FIG. 2b, however, once interposed between an anatomical mass 20 and an anatomical structure 18, such lattice structure 22 is caused to deform in amount corresponding to the degree of pressure (i.e., beyond the baseline amount of pressure) exerted by the structure against the mass. As illustrated, by virtue of being sandwiched between the structure 18 and mass 20, the degree of collapse is formed within the lattice 22 which corresponds to a fixed amount of pressure. Data indicative of the degree of compression will be fed to a monitor, discussed more fully below. As will be readily appreciated by those skilled in the art, the lattice structure 22 may be configured such that the same is operative to measure a degree of stress or pressure applied thereto without collapsing or otherwise collapse entirely once a predetermined amount of pressure is applied externally about the balloon-type sack 24. Moreover, by virtue of having fixed dimensions, it is further contemplated that the lattice structure 22 may be operative to measure spatial dimensions by determining various points of contact made about the balloon-type sack 24 encapsulating such lattice structure 22.

Figure 3B:
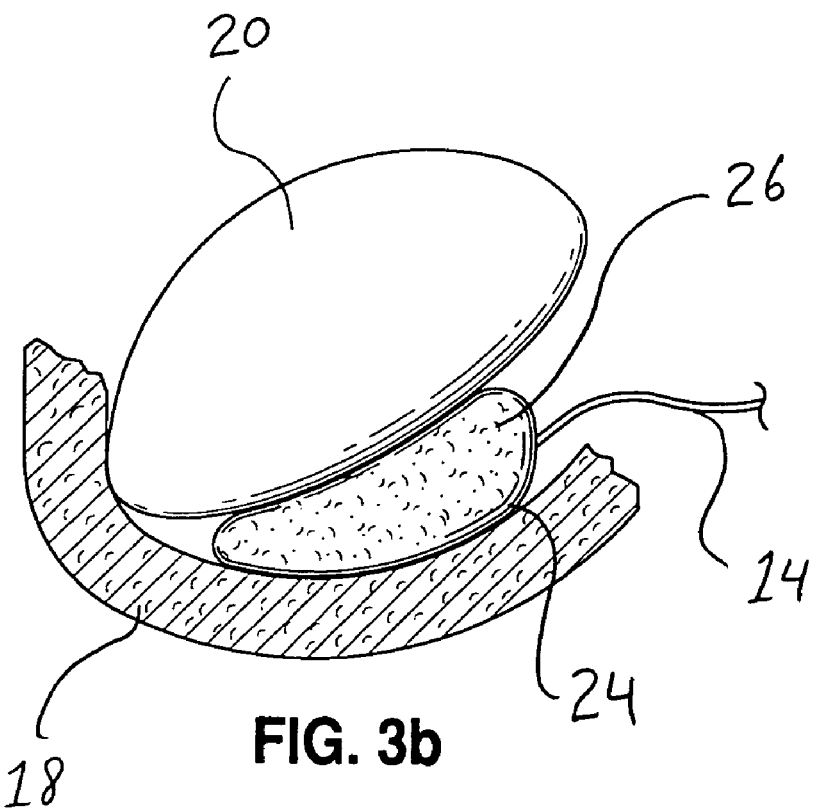
FIG. 3b is a perspective view of the sensor depicted in 3a shown assuming a compressed state as disposed between an anatomical mass and an anatomical structure.

In an alternative embodiment shown in FIGS. 3a-3b, the supportive material disposed within the balloon membrane 24, sensor 12 may comprise a sponge-like material 26, such as compressive-type foam, which is operative to assume a first expanded configuration, as depicted in FIG. 3a, when no pressure or a baseline amount of pressure is applied thereto, and assume a second compressed configuration shown in FIG. 3b once a requisite amount of pressure is applied externally thereabout, as imparted externally about the balloon membrane 24 encapsulating such sponge-like material 26. It is contemplated that such sponge-like material 26 will be operative to selectively collapse to a degree corresponding to the degree of pressure exerted thereabout. In this regard, due to the compressive force imparted to such sponge-like material disposed within the sensor, the same is thus caused to correspondingly compress to a degree indicative of the pressure or tension imparted thereto. Alternatively, the sponge-like material 26 may be operative to measure the amount of stress or pressure applied thereto without deforming or otherwise be configured to measure spatial relationships between two or more anatomical masses/structures or within an anatomical mass/structure.

In yet a further embodiment, the sensor may simply comprise the combination of a balloon coupled to a gas or fluid-filled syringe (not shown). The balloon may preferably be pre-filled or, at the time of a given procedure, filled to a certain volume using the syringe to establish a baseline pressure.

Figure 4:
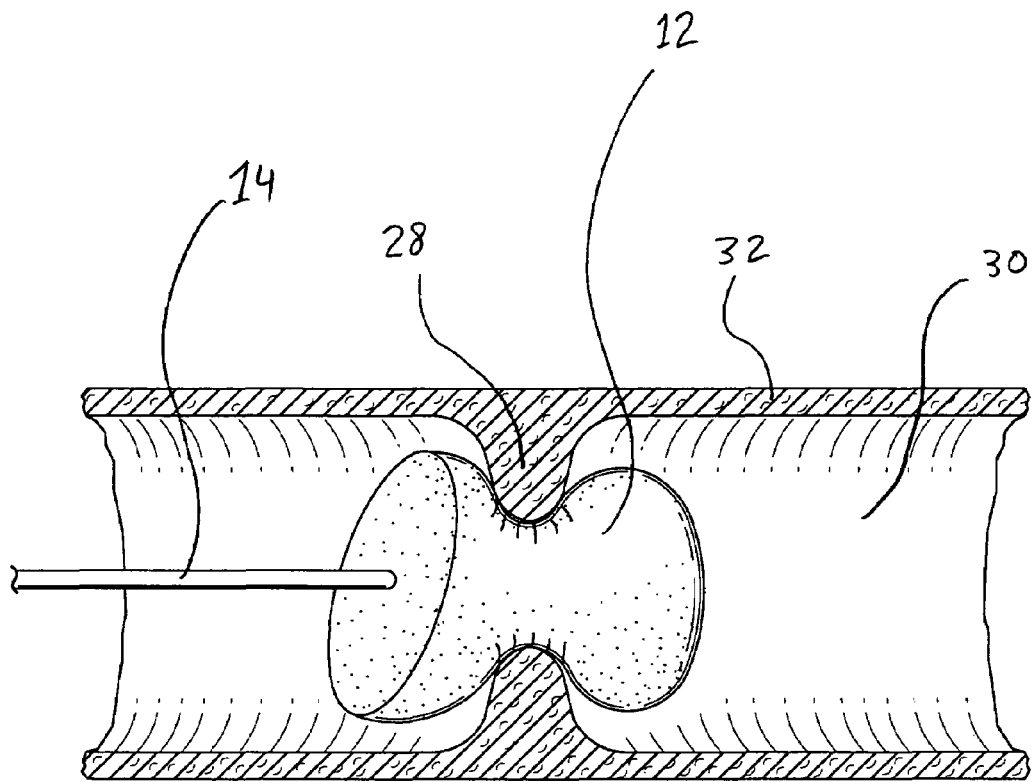
FIG. 4 is a perspective view, shown partially in cross-section, of a sensor constructed in accordance with a preferred embodiment shown disposed within the lumen of an anatomical structure and axially positioned within a sphincter-type muscle.

In addition to applications where the sensor is interposed between two objects to measure the compressive force therebetween, the sensor 12 of the present invention may further be operatively configured to measure a compressive force as exerted within the lumen of a tube or as imparted by a sphincter muscle. As illustrated in FIG. 4, the sensor 12 is shown being positioned within a tube surrounded by a sphincter-type muscle 28, the latter being disposed within the lumen 30 of a tube 32. As shown, the sensor 12 is operative to measure sphincter tone or otherwise measure compressive force exerted within the lumen 30 of the tube 32. Along these lines, it is contemplated that such sensor 12 may be adapted for intraurethral, intraanal, intravesical, intraesophageal, and intravascular applications where it is desired to measure physiological pressures at such target sites. In this regard, it is expressly contemplated that such sensor 12 will be operative to measure intraesophageal pressure, as is desired to measure the competency of the esophageal sphincter, as well as for intra-urethral and intraanal applications to assess sphincter tone as should be evaluated in the diagnosis of urinary or fecal incontinence. In related applications, it is contemplated that the sensor may be operative to impart physiological pressure measurements related to fluid flow, such as blood flow and intravascular pressure and urethral resistance to outflow of urine.

Figure 5:
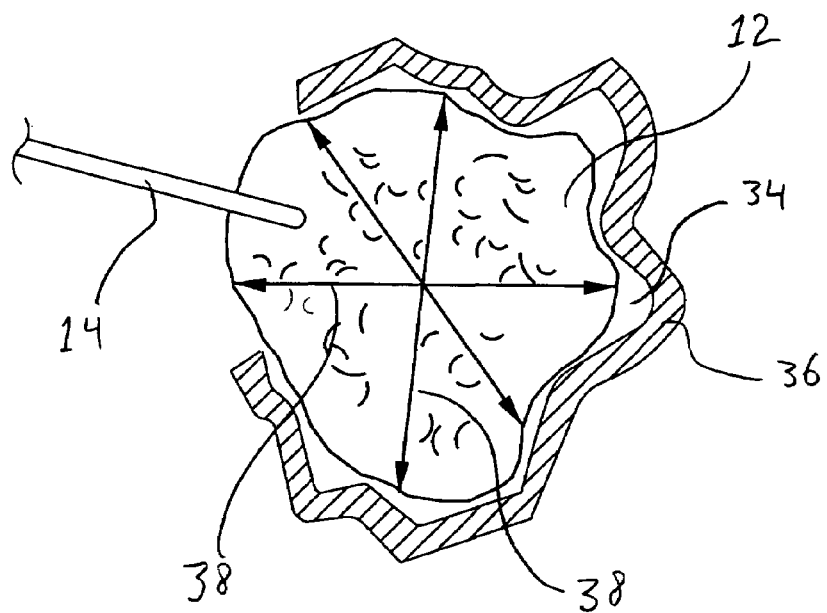
FIG. 5 is a perspective view, shown partially in cross section, of a sensor as positioned within an intramuscular compartment and operative to provide pressure or dimensional measurements therewithin.

It is further contemplated that the sensor 12 may be operative to provide data indicative of the spacing within a lumen or the volume within a cavity. In such applications, as illustrated in FIG. 5, it is contemplated that the sensor 12 may be operatively positioned within a cavity defined by an anatomical structure 36 and thereafter caused to expand or contract, depending upon the particular application, until the specific dimensions, contours, and/or volume of the target site, represented generally as 38, are determined. Such data will correspond to the external dimensions and parameters of the sensor 12, as may be determined via a variety of mechanisms well-known in the art. To that end, it is contemplated that the sensor may be configured to either incrementally decrease in volume, as per embodiments discussed above regarding the lattice and sponge-type sensors or, alternatively, utilize an expandable sensor, such as an air or fluid-filled balloon that is operative to cause the sensor to conform about the anatomical structure within which the same is positioned. Alternatively, in certain applications, such as applications involving the measurement of pressure exerted within an intramuscular compartment, the sensor 12 may be operative to merely identify in the fluctuations in the change of pressure exerted thereabout.

In any such application, it is contemplated that the data derived from the sensor will be operative to provide diagnostic information, such as degree of stenosis within the lumen of a vessel or volumetric or pressure changes within an intramuscular compartment, that will be operative to assist a physician in evaluating a particular condition.

In addition to applications related to diagnostic purposes, the systems and methods of the present invention are operative to assess physiological pressures and spatial relationships during surgical procedures, and in particular the fixation of anatomical structures into position according to a specific placement and orientation in order to achieve a favorable patient outcome. Along these lines, it is expressly contemplated that the procedures and methods of the present invention may be deployed during surgical procedures such as pubovaginal sling surgery when placement and tension of an anatomical structure, namely a sling or graph, is tied or fixed into place. In this respect, it is contemplated that in such applications a sensor 12, as constructed in any of the aforementioned embodiments, will be operative to measure the spatial separation and/or the compression of an anatomical structure upon an anatomical mass as the structure is affixed into position within the patient. In such applications, however, it is contemplated that the sensor 12 need not be limited to applications where the same must necessarily be interposed between the anatomical structures, but may be affixed or positioned anywhere upon such anatomical structures at any point therealong, so long as the tension, pressure and/or spatial relationship between such structures can be sufficiently measured and identified by such sensor device.

In any of the aforementioned applications, whether diagnostic or surgical, the sensor 12 will be coupled to a meter or monitor, such as 16 depicted in FIG. 1, that provides an indication as to the degree of tension and/or pressure being exerted in the applicable context (i.e., between structures, within a lumen, during surgical fixation) based upon signals received from the sensor. Such signals may likewise be utilized to correlate the spatial relationship between target anatomical structures or tissue masses. For example, in the lattice and sponge embodiments discussed above, it is contemplated that external deformation of the balloon-type sack 24 can serve a basis for determining the spatial relationship between the sling and the anatomical structure. As discussed above, it is contemplated that external deformation may be quantitatively measured as distance or space within the balloon or sack is proportionately increased or decreased. As a consequence, the devices of the present invention may further be capable of providing an indication to monitor the spatial distance or separation between anatomical structures. In all such applications, however, it will be understood that the monitor 16 will be able to provide a measurement indicative of the properties (i.e., pressure, stress or distance) sought to be identified. To that end, it should be understood that the monitor 16 may take any suitable monitor operative to impart such data known or later developed in the art, and can include any type of modular or portable component that may be operative to provide generalized measurements for a variety of procedures or specific measurements for a particular type of procedure. Such monitor 16 may further be configured to either single or repetitive usage.

In addition to providing data indicative of a particular patient or procedure, it is further contemplated that the devices of the present invention may further make a comparative analysis between the spacing and/or pressure being measured in relation to a given structure and spacing and/or tension parameters that have been derived from a database corresponding to physiological spacing and/or pressure levels that have been ascertained from a determined patient population having been diagnosed and/or have undergone the relevant surgical procedure. In this regard, it is contemplated that the present invention may further incorporate the use of a microprocessor or signal processor (not shown) that processes the signal received from the sensor and makes a comparison to such established pressure or spatial parameters to thus provide the physician with an indication of not only what pressure and/or spacing is being experienced by a patient or structure during a given procedure, but also whether such pressure and/or spacing is normal or abnormal, or is indicative of a favorable post-operative outcome, namely, that the target anatomical structure/tissue mass will be sufficiently supported and positioned.

To derive such spatial and/or pressure parameters, it is understood that it may be necessary to accumulate a statistically significant number of readings from a sufficiently large population of patients having undergone the relevant diagnostic and/or surgical procedures before such spatial parameters can be established. Alternatively, such spatial and/or pressure parameters indicative of normal or abnormal conditions and/or of favorable post-operative outcomes may be determined based upon certain physiological characteristics of the patient being diagnosed or undergoing surgery, or may even comprise simple threshold levels estimated to produce the desired post-operative outcome. Notwithstanding, once such parameters have been established, it is contemplated that the systems and methods of the present invention will be capable of providing the physician with a signal corresponding to a measured physiological pressure for use in making a diagnosis or otherwise providing data useful in performing a specific surgical procedure.

Along these lines, it is contemplated that the sensor 12 may likewise be adapted to exclusively measure the distance or spacing between anatomical structures and masses. In this respect, and as opposed to measuring tension and pressure exerted against a target anatomical mass/structure, optimal placement may be predicated upon the implant, tissue, graft or sling having a desired degree of slack or sag, and hence, may not readily produce a measurable tension, let alone supportive pressure against the anatomical structure that is consequently produced thereby. In such applications, it is contemplated that such sensor 12 may take the form of a balloon-type sensor, as discussed above, whereby the spatial distance or forces between anatomical structures/masses may be measured as a function of either the volume in the balloon, or alternatively, the internal pressure within the balloon.

As per all the aforementioned embodiments, the present invention can be specifically designed and adapted for use in a wide variety of clinical applications, and specifically tailored to obtain measurements and physiological data corresponding to the specific anatomical structure/mass or a particular patient, as well as obtain data related thereto indicative of normal or abnormal conditions. Accordingly, the present invention should be construed as broadly as possible to encompass all foreseeable applications.

Additional modifications and improvements of the present invention may also be apparent to those skilled in the art. Thus, the particular combination of the parts described and illustrated herein is intended to represent only one embodiment of the present invention, and is not intended to serve as limitations of alternative devices within the spirit and scope of the invention. Moreover, it should be understood that all of the embodiments disclosed herein may find use in a wide variety of clinical and surgical procedures other than these procedures discussed herein. For example, it will be readily recognized that the specific embodiments may find widespread use in the diagnosis of medical conditions involving numerous other specialties as well as numerous surgical procedures involving orthopedic surgery and/or cosmetic or reconstructive surgery. Accordingly, it is to be understood that the present invention is in no way to be deemed limited thereto.

What is claimed is:

1. A device for determining a pressure exerted within an anatomical structure, said device comprising:
   a) a sensor comprising an encapsulated member having (i) a membrane enclosing an encapsulated volume therewithin and (ii) a body of supportive material disposed within the membrane that substantially fills and defines the encapsulated volume, the sensor having a link extending therefrom, said sensor being positionable within the anatomical structure, said sensor being operative to compress against said anatomical structure, measure pressure exerted within said anatomical structure, produce a signal representative of the pressure exerted within said anatomical structure and transmit said signal through said link; and
   b) a monitor coupled to said link for receiving said signal generated by said sensor, said monitor being operative to provide a quantifiable indication of the compressive force exerted within said anatomical structure,
   wherein the supportive material is compressive foam disposed within the encapsulated member, said compressive foam being operatively transitional between a first expansive state when a first baseline amount of pressure is applied thereto and a second compressed state whereby said foam compresses to assume a configuration having a reduced volume corresponding to a second higher amount of pressure applied upon the external surface of said encapsulated member.

2. The device of claim 1 wherein said foam is operative to incrementally decrease in volume when a correspondingly incremental increase in pressure is applied to the external surface of said encapsulated member.

3. The device of claim 1 wherein said member is encapsulated within a balloon-type sack.

4. A device for determining an amount of pressure exerted between a first anatomical structure and a second anatomical structure, said device comprising:
   a) a sensor configured to be interposed between said first and second anatomical structures, said sensor comprising an encapsulated member having (i) a membrane enclosing an encapsulated volume therewithin and (ii) a body of supportive material disposed within the membrane that substantially fills and defines the encapsulated volume, the sensor having a link extending therefrom, said sensor being compressible against said first anatomical structure and said second anatomical structure, wherein said sensor is operative to measure the compressive force exerted between said first anatomical structure and said second anatomical structure, produce a signal representative of the compressive force and transmit said signal through said link; and
   b) a monitor coupled to said link for receiving said signal generated by said sensor, said monitor being operative to provide a quantifiable indication of the compressive force between said first anatomical structure and said second anatomical structure,
   wherein the supportive material is compressive foam disposed within the encapsulated member, said compressive foam being operatively transitional between a first expansive state when a first baseline amount of pressure is applied thereto and a second compressed state whereby said foam compresses to assume a configuration having a reduced volume corresponding to a second higher amount of pressure applied upon the external surface of said encapsulated member.

5. The device of claim 4 wherein said foam is operative to incrementally decrease in volume when a correspondingly incremental increase in pressure is applied to the external surface of said member.

6. The device of claim 4 wherein said member is encapsulated within a balloon-type sack.

7. A device for determining a pressure exerted within an anatomical structure, said device comprising:

a sensor comprising an encapsulated member having (i) a membrane enclosing an encapsulated volume therewithin and (ii) a body of supportive material disposed within the membrane that substantially fills and defines the encapsulated volume, the sensor being positionable within an anatomical structure, wherein said sensor operative to compress against said anatomical structure, measure pressure exerted within said anatomical structure, and produce a signal representative of the pressure exerted within said anatomical structure, wherein said sensor is adapted to be coupled to a monitor for receiving said signal generated by said sensor, said monitor being operative to provide a quantifiable indication of the compression force exerted within said anatomical structure, and wherein the supportive material is compressive foam disposed within the encapsulated member, said compressive foam being operatively transitional between a first expansive state when a first baseline amount of pressure is applied thereto and a second compressed state whereby said foam compresses to assume a configuration having a reduced volume corresponding to a second higher amount of pressure applied upon the external surface of said encapsulated member.

8. A device for determining an amount of pressure exerted between a first anatomical structure and a second anatomical structure, said device comprising:

a sensor configured to be interposed between said first and second anatomical structures, said sensor comprising an encapsulated member having (i) a membrane enclosing an encapsulated volume therewithin and (ii) a body of supportive material disposed within the membrane that substantially fills and defines the encapsulated volume, said sensor being compressible against said first anatomical structure and said second anatomical structure, wherein said sensor is operative to measure the compressive force exerted between said first anatomical structure and said second anatomical structure, and produce a signal representative of the compressive force, wherein said sensor is adapted to be coupled to a monitor for receiving said signal generated by said sensor, said monitor being operative to provide a quantifiable indication of the compressive force between said first anatomical structure and said second anatomical structure, and wherein the supportive material is compressive foam disposed within the encapsulated member, said compressive foam being operatively transitional between a first expansive state when a first baseline amount of pressure is applied thereto and a second compressed state whereby said foam compresses to assume a configuration having a reduced volume corresponding to a second higher amount of pressure applied upon the external surface of said encapsulated member.

* * * * *